United States Patent
Asada et al.

(10) Patent No.: US 6,828,107 B2
(45) Date of Patent: Dec. 7, 2004

(54) IMMUNOASSAY METHOD FOR BNP

(75) Inventors: Hidehisa Asada, Takatsuki (JP); Hiroyuki Shimizu, Kobe (JP); Kazuaki Endou, Takatsuki (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/508,435

(22) PCT Filed: Sep. 10, 1998

(86) PCT No.: PCT/JP98/04063

§ 371 (c)(1),
(2), (4) Date: Mar. 13, 2000

(87) PCT Pub. No.: WO99/13331

PCT Pub. Date: Mar. 18, 1999

(65) Prior Publication Data

US 2003/0157596 A1 Aug. 21, 2003

(30) Foreign Application Priority Data

Sep. 11, 1997 (JP) .............................................. 9/246684

(51) Int. Cl.[7] .............................................. G01N 33/53
(52) U.S. Cl. ....................................... 435/7.1; 435/975
(58) Field of Search .................................. 435/975, 7.1

(56) References Cited

FOREIGN PATENT DOCUMENTS

WO   93/24531   12/1993

OTHER PUBLICATIONS

Harlow et al. Antibodies: A Laboratory Manual, p. 579, 1988.*
Hunt et al. Biochemical and Biophysical Research Communication, vol. 214, No. 3, 1175–1183, 1995.*
FEBS Letters, vol. 400, No. 2, pp. 177–182, (1997), particularly p 178 2.2.
Y. Sawada et al., "Co–Elevation of Brain Natriuretic Peptide and Proprotein–Processing Endoprotease Furin after Myocardial Infarction in Rats", FEBS Letters, vol. 400, No. 2, pp. 177–182, 1997.

* cited by examiner

*Primary Examiner*—Patrick J. Nolan
(74) *Attorney, Agent, or Firm*—Wenderoth, Lind & Ponack, L.L.P.

(57) ABSTRACT

An immunoassay specific for mammalian γ-BNP derivatives, which uses the first antibody reactive with mammalian α-BNP and the second antibody reactive with mammalian prepro-BNP or γ-BNP derivatives and not α-BNP, and at least one of the first and the second antibodies is optionally labeled detectably labeled or immobilized.

20 Claims, 5 Drawing Sheets

IMMUNOASSAY METHOD FOR BNP

This is a 371 of PCT/JP98/04063, filed Sep. 10, 1998.

TECHNICAL FIELD

The present invention relates to an immunoassay for the brain natriuretic peptide (BNP) which is a member of natriuretic peptide family, more specifically, it relates to an immunoassay for γ-BNP and derivatives thereof.

BACKGROUND ART

Natriuretic peptide family includes three members, i.e., atrial natriuretic peptide (ANP), brain natriuretic peptide (BNP) and type C natriuretic peptide (CNP). Among them, ANP and BNP are cardiac hormones which are mainly biosynthesized in and secreted from the heart. ANP and BNP are similar in structure. ANP is a peptide of 28 amino acids with a ring (circular) structure formed by a disulfide bond between the 7th and the 23rd cysteine residues, while BNP is a peptide of 32 amino acids with a ring structure formed by a disulfide bond between the 10th and the 26th cysteine residues. These mature peptides of 28 and 32 amino acids have been considered to be produced from respective precursor when a leader sequence is cleaved off intracellularly or at the time of secretion. That is, there has been reported that human BNP is first synthesized as a preprohormone (hereinafter, referred to as prepro-BNP) in myocardial cells, which is split before or at the time of secretion between $Ser^{26}$-$His^{27}$ to give pro-BNP (hereinafter, referred to as γ-BNP), and which is further split between $Arg^{102}$-$Ser^{103}$ to give BNP-32 (hereinafter, referred to as α-BNP) and BNP (1–76), and that the former exhibits the activity. It has been considered that at least the ring structure must be remained for the expression of activity.

The secretion of cardiac hormones being stimulated by various heart diseases, it well reflects the change in the cardiac functions. The secretion of ANP is accelerated mainly when the atrium undergoes a load, while the biosynthesis and secretion of BNP are stimulated when the ventricle undergoes a load. Accordingly, both ANP and BNP are useful as indicators in the diagnosis of heart disease. As the progress of investigation in the in vivo role of respective hormone, the advantageous features of BNP as an indicator for diagnosing heart disease have become clear. For example, the blood concentration of BNP is only ⅙ of ANP in a normal subject but it becomes higher than ANP in patients of heart failure or the like; the blood concentration of BNP increases in the case of heart failure like ANP, and the plasma concentration of BNP often exceeds that of ANP reflecting more accurately the severity of heart dysfunction; the plasma concentration of both ANP and BNP elevates in peripheral blood and elevation rate is higher in BNP. Moreover, BNP level in patients of heart failure sometimes increases to several tens times to several hundreds times of that of healthy normal subjects, and the change of BNP in the cases of heart failure is so marked that no other hormones are incomparable therewith. For these reasons, the usefulness of BNP measurement has been suggested (Y. Saito et al., Mebio, 12(5), 28, 1995).

Under the conditions, an immunoassay which utilizes anti-BNP antibody and is applicable to the diagnosis of cardiac insufficiency has been proposed. Japanese Patent Publication (KOHYO) 7-507210 describes a method of measuring γ-BNP (1–76) produced by biodegradation by protease or the like. However, this method is directed to γ-BNP (1–76) which lacks the portion(s) essential for the expression of activity such as ring structure and, therefore, cannot determine the hormone activity directly.

An assay kit for the measurement of α-BNP having natriuretic activity has been marketed ("BNP-32", Peninsula). With this kit, degradation products of α-BNP in blood including fragments lacking activity due to the deletion of C-terminal region can also been measured. Taking the low blood concentration of BNP into consideration, the measurements involving the degradation products cannot be disregard. Accordingly, the said method connotes disadvantages to be an assay for BNP in th establishment of an accurate diagnosis of heart failure.

As a kit for the measurement of BNP free from the disadvantages above has been marketed ("SHIONORIA BNP", Shionogi), which characteristically uses an antibody recognizing the structure essential for the expression of activity. However, this method would be affected significantly by the process for collecting and storing blood sample, because α-BNP is extremely instable in collected blood. It is, therefore, suggested that the sample should be specifically treated by, for instance, adding an agent for inhibiting degradation into a blood collecting tube or maintaining the sample at low temperature so as to obtain reliable data. Such procedures may hamper the extensive clinical application of the said BNP assay kit.

DISCLOSURE OF INVENTION

The present inventors have conducted research intensively for the purpose of establishing an accurate method of diagnosing cardiac diseases involving BNP and found that BNP exists in blood in the form of γ-BNP or its degradation product which at least comprises structurally the α-BNP moiety (hereinafter, they are referred to as "γ-BNP derivative"), and not in the form of α-BNP which has so far been considered to be dominant. The inventors have also found that γ-BNP is more stable than α-BNP in blood, that is, one role of the N-terminal structure of γ-BNP, among many, would be the stabilization of BNP. The above indicates that an organism biosynthesizes at least 2 kinds of BNP molecule which share the BNP activity but differ in half-life. These findings led the present inventors to have a view that it is indispensable to establish a method specific for not only α-BNP but also γ-BNP to accomplish an accurate diagnosis of cardiac diseases.

The present invention provides an immunoassay specific for mammalian γ-BNP derivatives, characterized in that it uses the first antibody which is reactive with mammalian α-BNP and the second antibody which is reactive with mammalian prepro-BNP or γ-BNP derivatives and not reactive with α-BNP.

As used herein, the term "mammalian α-BNP" refers to a peptide of low molecular weight having natriuretic activity which is derived from mammalian prepro-BNP or γ-BNP through the removal of N-terminal region as a result of processing at the carboxy terminus of processing signal sequence. In case of human BNP, α-BNP is a peptide consisting of C-terminal 32 amino acids (Nos. 103–134) of the amino acid sequence of SEQ ID NO: 1 and having a ring structure. The carboxy terminus of processing signal sequence on the prepro-BNP molecule varies slightly depending on the species. For example, it is No. 102 Arg in case of human BNP while it is No. 100 amino acid in case of porcine or canine BNP.

As used herein, the term "mammalian γ-BNP" refers to a pro-BNP comprising a partial peptide of 32 amino acids corresponding to α-BNP at the carboxy terminal region. In case of human γ-BNP, it is pro-BNP of 108 amino acids from No. 27 His to No. 134 His of the amino acid sequence of SEQ ID NO: 1. The term "prepro-BNP" refers to a peptide of 134 amino acids from No. 1 Met to No. 134 His of the amino acid sequence of SEQ ID NO: 1 in case of human.

As used herein, the term "mammalian γ-BNP derivative" refers to a peptide fragment derived from mammalian prepro-BNP or γ-BNP through mainly the in vivo protease reaction, which fragment includes or is larger than α-BNP. Although γ-BNP derivative would comprise a molecule of the same or smaller size compared to γ-BNP in general, it may comprise a molecule larger than γ-BNP. Otherwise specifically mentioned, as used herein, the term "γ-BNP derivative" includes γ-BNP itself.

The term "stable", when used herein in connection with BNP, means that a BNP molecule maintains the C-terminal ring structure including C-terminus of BNP and the natriuretic activity after undergoing the degradation by protease, and that the said activity is not significantly decreased even 24 hours from the collection of blood samples. In light of this definition, the γ-BNP derivative as the target substance (analyte) of the present immunoassay is stable.

On the other hand, the term "unstable" means that a BNP sample undergoes degeneration by protease at the C-terminal region and that the natriuretic activity is significantly decreases 24 hours from the collection of blood samples. In light of this definition, α-BNP is unstable.

BRIEF DESCRIPTION OF DRAWINGS

In FIG. 1, A indicates the position of elution of α-BNP.

In FIG. 2, A indicates the position of elution of α-BNP.

In FIG. 3, A indicates the position of elution of α-BNP.

BEST MODE FOR CARRING OUT THE PRESENT INVENTION

Figure 1:
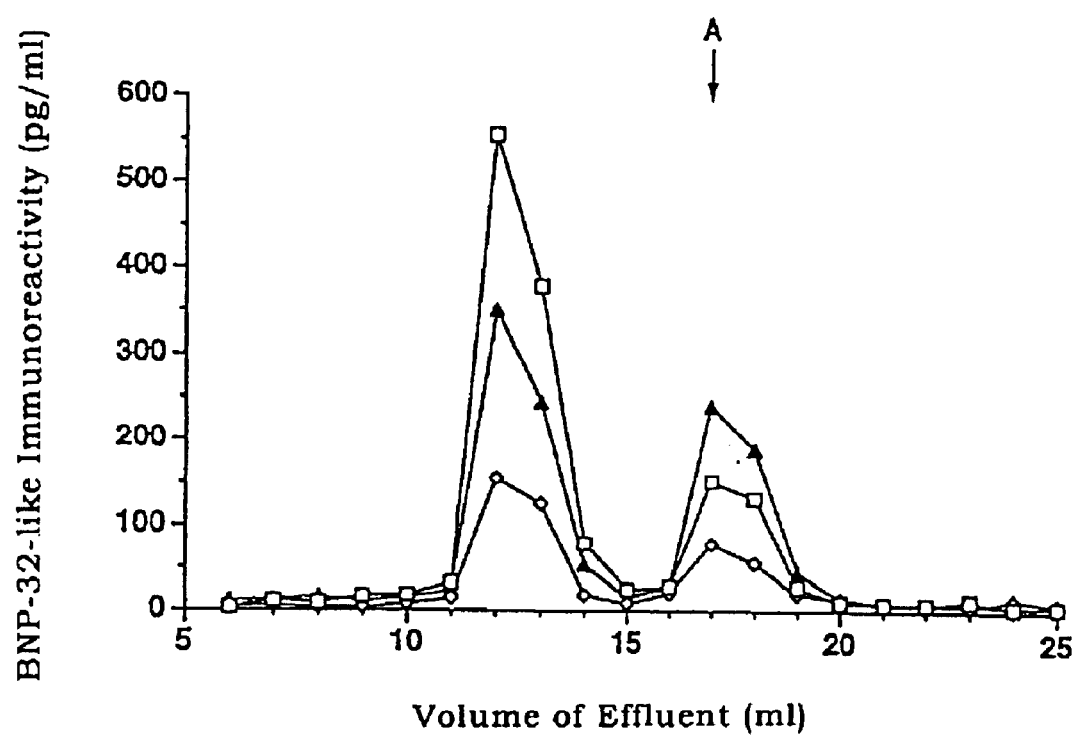
FIG. 1 is a chromatogram obtained in an α-BNP assay system wherein gel filtration HPLC was conducted using Superdex 75 in a plasma sample.

In one embodiment of the present invention, it is related to a method which uses two antibodies, wherein the first antibody is reactive with mammalian α-BNP and the second antibody is reactive with prepro-BNP or γ-BNP derivatives and is not reactive with α-BNP.

Antibodies used in the present method can be monoclonal or polyclonal antibodies. The first antibody can be prepared according to a method known in the art using as an antigen human α-BNP which is commercially available or chemically synthesized, or a partial peptide thereof. Alternatively, a monoclonal antibody appended to a commercially available α-BNP assay system (kit) for measuring α-BNP ("SHIONORIA", Shionogi) is also available, which is reactive with the C-terminal region of α-BNP.

As the second antibody, any antibody can be used subject that it meets the conditions above. Preferred examples of such antibody include those specific for the amino acid sequence shown by the amino acid Nos. 27–102 of SEQ ID NO: 1 or metabolites thereof. The γ-BNP derivatives as an analyte to be measured by the present method preferably include at least the partial amino acid sequence shown by the amino acid Nos. 27–134 of SEQ ID NO: 1, in case of human BNP. Accordingly, in a preferred embodiment of the present invention, a special attention is preferably paid in the selection of an antigen to obtain an antibody capable of recognizing the amino acid sequence shown by amino acid Nos. 27–102. The preparation of such an antibody can be carried out by any one of methods known in the art. Theoretically, γ-BNP molecule can be cleaved by protease at sites corresponding to No. 47 (Arg), No. 53 (Lys) and No. 72 (Arg) in the amino acid sequence of SEQ ID NO: 1, and, therefore, an antibody recognizing an amino acid sequence shown by amino acid Nos. 73–102 of SEQ ID NO: 1 can be used as the second antibody.

The assay of the present invention can be either a competitive- or sandwich-assay and an antibody to be used may be a monoclonal- or polyclonal-antibody.

At least one of the first and the second antibodies may be labeled detectably or immobilized on a solid support.

The method for labeling or immobilizing an antibody is known to one ordinary skilled in the art. Examples of label include without limitation radioactive isotopes, enzymes, fluorescent substances, luminescent substances, and particles. The labeling of an antibody can be carried out according to a method known to one ordinary skilled in the art, for example, that described by Kono et al. (Kaku-Igaku Gijutu, 13(1), 2, (1993)).

The present invention further provides a kit for immunoassay specific to mammalian γ-BNP derivatives, characterized in that it comprises two antibodies wherein the first antibody is reactive with mammalian α-BNP and the second antibody is reactive with mammalian prepro-BNP or γ-BNP derivatives and is not reactive with α-BNP.

The kit of the present invention can be for a competitive- or sandwich-assay and an antibody to be used may be a monoclonal- or polyclonal-antibody.

At least one of the first and the second antibodies may be labeled detectably or immobilized on a solid support. The kit of the present invention may further contain a means for detecting the label. Examples of label include without limitation radioactive isotopes, enzymes, fluorescent substances, luminescent substances, or particles.

The following examples and test examples are provided to further illustrate the present invention, without limiting the scope thereof.

EXAMPLE 1

Measurement of γ-BNP Derivatives by Sandwich IRMA

Throughout the following Examples, the ordinary reagents used are of special grade supplied by Wako Pure Chemicals Industries, Ltd. or Nacalai Tesque, Inc. The bovine serum albumin (BSA) was purchased from Sigma.

(1) Preparation of Plasma Sample

1) Venous blood was collected from patients of cardiac disease or healthy volunteers and placed in blood-collecting tubes containing EDTA and aprotinin (500 KIU/1, Sigma) derived from bovine lung. The tubes were centrifuged (×2000 g at 4° C.) for 5 minutes with H-107RGA (Kokusan) to separate blood cells. The resultant plasma samples were freezed and stored at −80° C. until use.

2) The plasma samples prepared in 1) above from patients of cardiac disease or healthy volunteers were fractionated by gel filtration HPLC system LC10A (Shimadzu) equipped with Superdex 75 10/30 column (Pharmacia). After equilibrating the column with 0.1 M phosphate buffer (pH 7.5, 0.3M NaCl, 5 mM EDTA) at flow rate of 1 ml/min, 1 ml of plasma sample was injected and 1 ml each of effluent eluted from the column was collected. Each fraction was subjected to the measurement by assay systems for measuring α-BNP or γ-BNP as described in (2)-2 and (2)-3 below, respectively.

(2) Construction of Assay System For Measuring α-BNP- or γ-BNP Derivative

1) In the assay system, the following peptides, antibodies and kits were used.

Human α-BNP (Peptide Institute)

Antibody against the amino terminal region of γ-hBNP (amino acid Nos. 27–64 of SEQ ID NO: 1) (Peptide Institute)

Monoclonal antibody against the carboxy terminal structure of α-BNP (BC203). BC203 is an immobilized antibody appended to SIONORIA BNP kit (Shionogi), wherein a monoclonal antibody directed to the carboxy terminal structure of α-BNP is immobilized on beads.

Monoclonal antibody against the ring structure of α-BNP (KYBNPII). KYBNPII is a monoclonal antibody appended to the SIONORIA BNP kit (Shionogi), which is directed to the ring structure (112–128) of α-BNP, and is labeled with $^{125}$I.

2) Measurement of Plasma Fraction by Assay System for α-BNP

The measurement of α-BNP was carried out by commercially available "SHIONORIA BNP kit" (Shionogi). The assay is based on sandwich IRMA (Immunoradiometric Assay) which uses a monoclonal antibody KYBNPII specific for the ring-structure of α-BNP and another monoclonal antibody BC203 specific for the carboxy terminal structure of α-BNP. The assay was carried out in accordance with the supplier's instructions.

Figure 2:
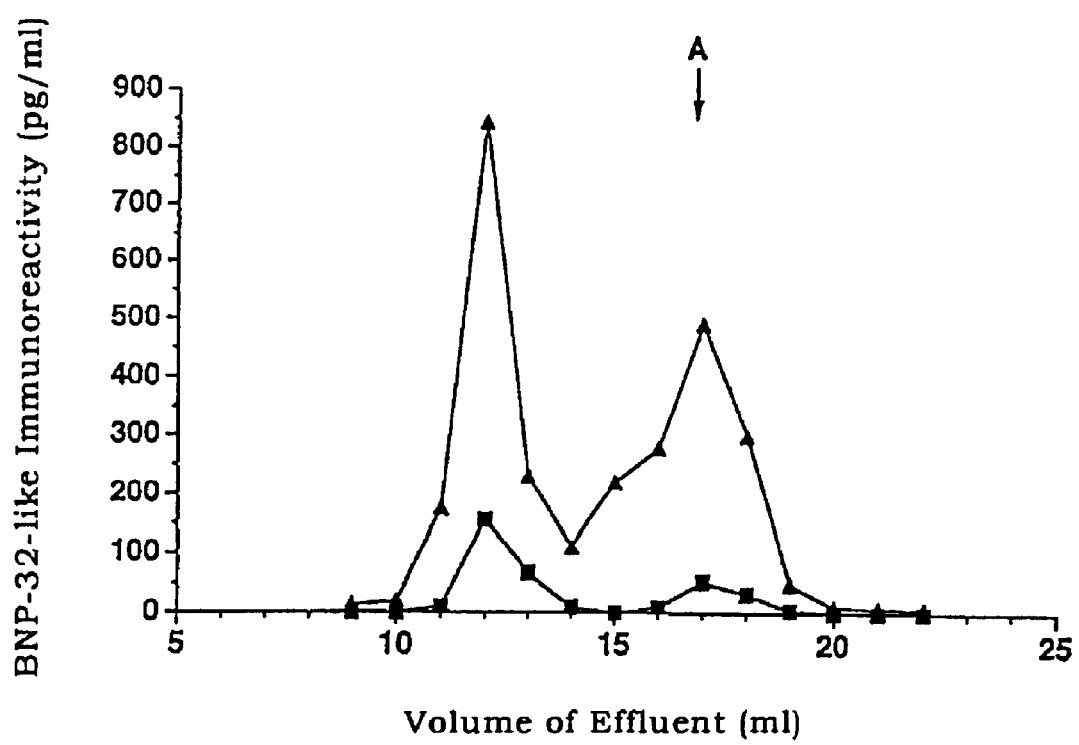
FIG. 2 is a chromatogram obtained in an α-BNP assay system wherein gel filtration HPLC was conducted using Superdex 75 in a plasma sample different from that shown in FIG. 1.

That is, 100 μl each of samples to be assayed or standard solutions (0, 4, 10, 150, 600 or 2000 pg/ml of α-BNP solution) were dispensed into a polystyrene test tube. To the test tube was added 200 μl of iodine-labeled anti-BNP antibody ($^{125}$I) solution, followed by one polystyrene bead on which anti-BC203 antibody has been immobilized. The mixture was stirred and allowed to react by leaving stand for 18 hours at 4° C. After washing twice with 2 ml of washing solution, radioactivity was measured on γ-counter ARC-600 (Aloka) The results are shown in FIGS. 1 and 2.

3) Measurement of Plasma Fraction by Assay System For γ-BNP Derivative

An antibody against amino terminal portion (Nos. 27–64) of γ-hBNP was first labeled with $^{125}$I.

IgG was purified from anti-serum (Peptide Institute) raised against amino terminal portion (amino acid Nos. 27–64 of SEQ ID NO: 1) of γ-hBNP using MASPII kit (Bio-Rad) and displaced with 0.5 M phosphate buffer (pH 7.5) using Centricon 30 (Amicon). The labeling of antibody was carried out by the chloramine T method. To a glass tube was dispensed 170 μl of purified IgG solution (77.6 μg, IgG), and 10 μl of Na$^{125}$I solution (34.2 MBq, Amersham) was added. After addition of 0.1% chloramine T solution (20 μl), the mixture was vigorously stirred at room temperature for 30 seconds. The reaction was quenched by adding 20 μl of 0.25% sodium pyrosulfite solution and 20 μl of 5% aqueous potassium iodide solution. When the reaction mixture was treated with Ampure SA column (Amersham) to remove unreacted $^{125}$I and to desalt, solution containing $^{125}$I-labeled antibody was obtained.

The sandwich IRMA was then carried out in plasma fractions by using the resultant antibody and polystyrene beads on which an antibody recognizing the carboxy terminal structure of α-BNP (BC203).

To a polystyrene tube was placed 100 μl each of samples to be assayed, followed by 200 μl of 0.1 M phosphate buffer (pH 7.5, 0.3M, 5 mM EDTA, 0.2% BSA and 500 KIU/1 bovine lung aprotinin (Sigma)) and one polystyrene bead on which BC203 antibody has been immobilized. The mixture was stirred and allowed to react by leaving stand for 18 hours at 4° C. After washing twice with 2 ml of washing solution, 300 μl of $^{125}$I-labeled antibody solution was added. The mixture was stirred and allowed to react by leaving stand for 18 hours at 4° C. After washing twice with 2 ml of washing solution, radioactivity was measured on γ-counter ARC-600 (Aloka) The results are shown in FIG. 3.

(3) Results

Figure 3:
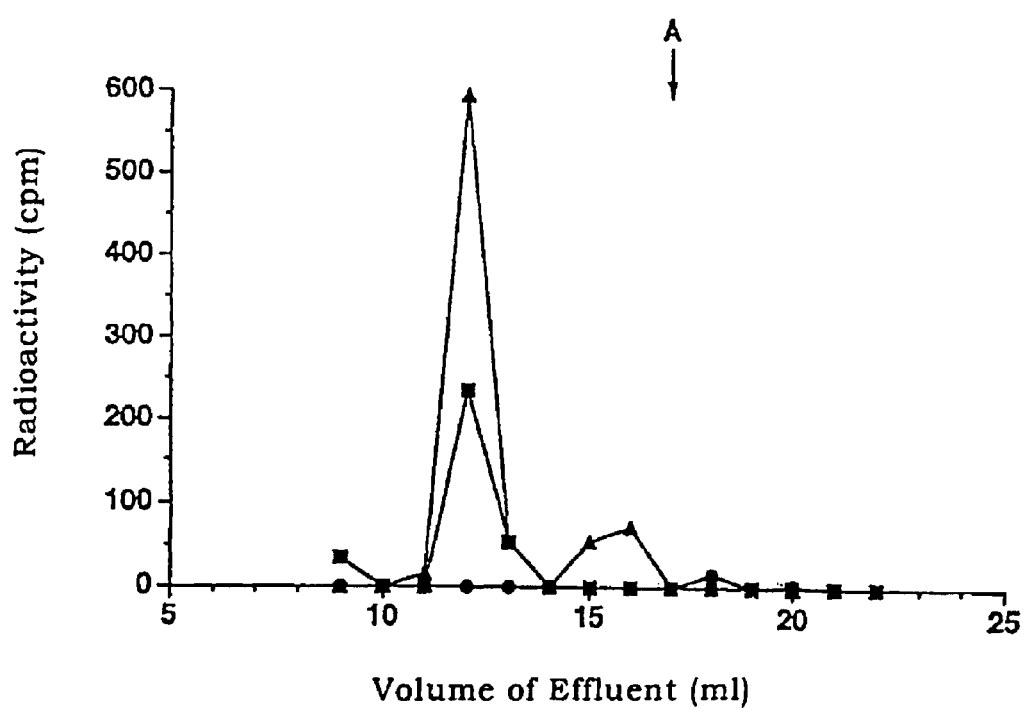
FIG. 3 is a chromatogram obtained in an immunoassay specific for γ-BNP wherein gel filtration HPLC was conducted using Superdex 75 in a plasma sample same as those shown in FIG. 2.

FIGS. 1, 2 and 3 show the chromatograms of gel filtration HPLC of plasma samples obtained from patients, wherein A is the position of elution of α-BNP.

FIG. 1 shows the result of the measurement conducted by the α-BNP assay kit described in (2)-2) above. In the FIG. 1, the vertical axis represents the concentration of BNP-like substances in each fraction and the horizontal axis the volume of effluent eluted from the column as measured by SHINORIA BNP kit. The solid triangle, open square, and open rhombus respectively represent the measurements in different plasma samples.

FIG. 2 shows the result of the measurement conducted by the α-BNP assay kit described in (2)-2) above in samples different from those shown in FIG. 1. In the FIG. 2, the vertical axis represents the concentration of BNP-like substances in each fraction and the horizontal axis the volume of effluent eluted from the column as measured by SHINO-RIA BNP kit. The solid triangle and solid square respectively represent the measurements in different plasma samples.

From FIGS. 1 and 2, it is revealed that there exist substances of molecular weight larger than α-BNP and having BNP-like immunoreactivity in the plasma of patients of cardiac disease, and that they are the major substances having BNP immunoreactivity.

FIG. 3 shows the results of the measurement conducted by γ-BNP assay kit described in (2)-3) above in the same samples those shown in FIG. 2. In FIG. 3, the vertical axis represents the radioactivity measured by the γ-BNP immunoassay system and the horizontal axis the volume of effluent eluted from the column. The solid circle represents the measurements of α-BNP, which obtained after fractionating human α-BNP solution by HPLC in a similar manner as described in the case of plasma.

From FIG. 3, it is revealed that the immunoassay specific for γ-BNP derivative of the present invention can detect the major substances with BNP immunoreactivity, but cannot α-BNP at all.

The results above indicate that the immunoassay for γ-BNP of the present invention is insensitive to α-BNP but specific to γ-BNP derivatives. Further, it has also been revealed that γ-BNP is the major substance having BNP immunoreactivity.

TEST EXAMPLE 1

Stability of γ-BNP Derivatives and α-BNP in Plasma

Fractions suspected to contain γ-BNP derivative were collected from those obtained by treating plasma samples collected from patients of cardiac disease by gel filtration HPLC. Venous blood was collected from healthy volunteers using blood-collecting tubes containing EDTA in the absence of bovine lung aprotinin. Plasma samples (the minimum detection limit of α-BNP<4 pg/ml) were prepared in a manner similar to that described in (1)-1) above. The plasma sample was allowed to stand for 0, 2, 6, 24 hours at room temperature (25° C.) after addition of the fraction. The stability of BNP derivative was evaluated by determining the BNP immunoreactivity in the plasma sample by means of SHIONORIA BNP kit for assaying α-BNP.

Separately, the stability of α-BNP was evaluated using a plasma sample prepared by adding chemically synthesized α-BNP to plasma collected from healthy volunteers and standing for 0, 2, 6 and 24 hours at 4° C. in the absence of bovine lung aprotinin as described above. The BNP immunoreactivity in the plasma sample was determined by SHIONORIA BNP kit in the same manner as above.

Figure 4:
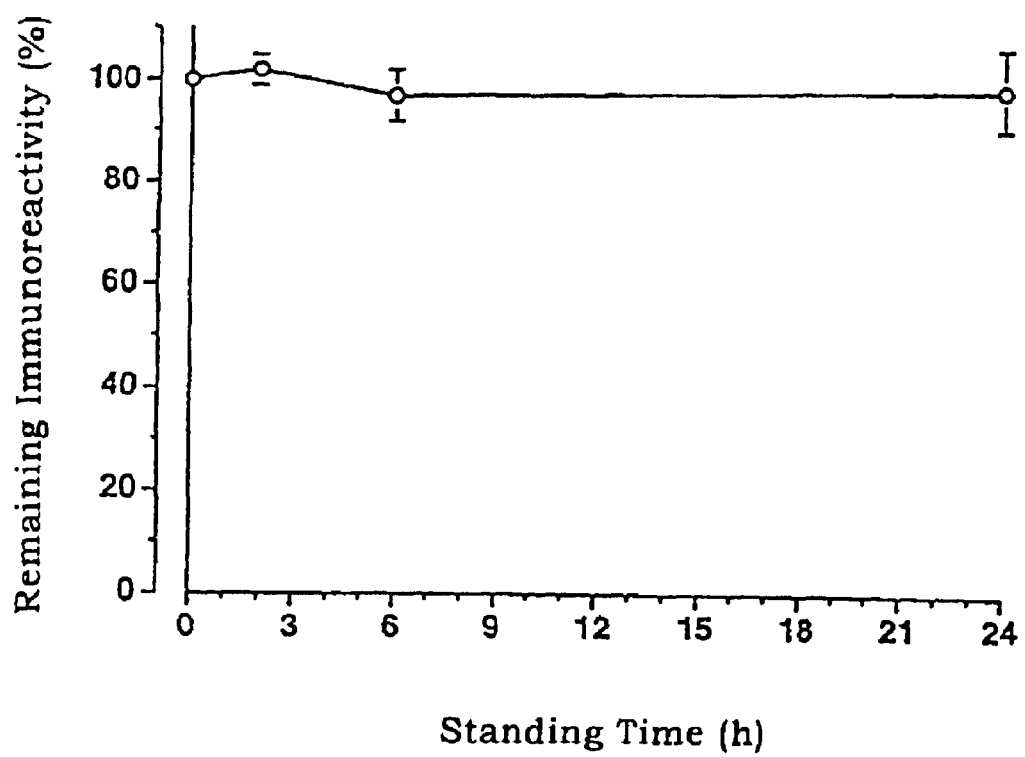
FIG. 4 is a graph showing the relationships between the storing time and BNP immunoreactivity of γ-BNP kept in human plasma at 25° C.
Figure 5:
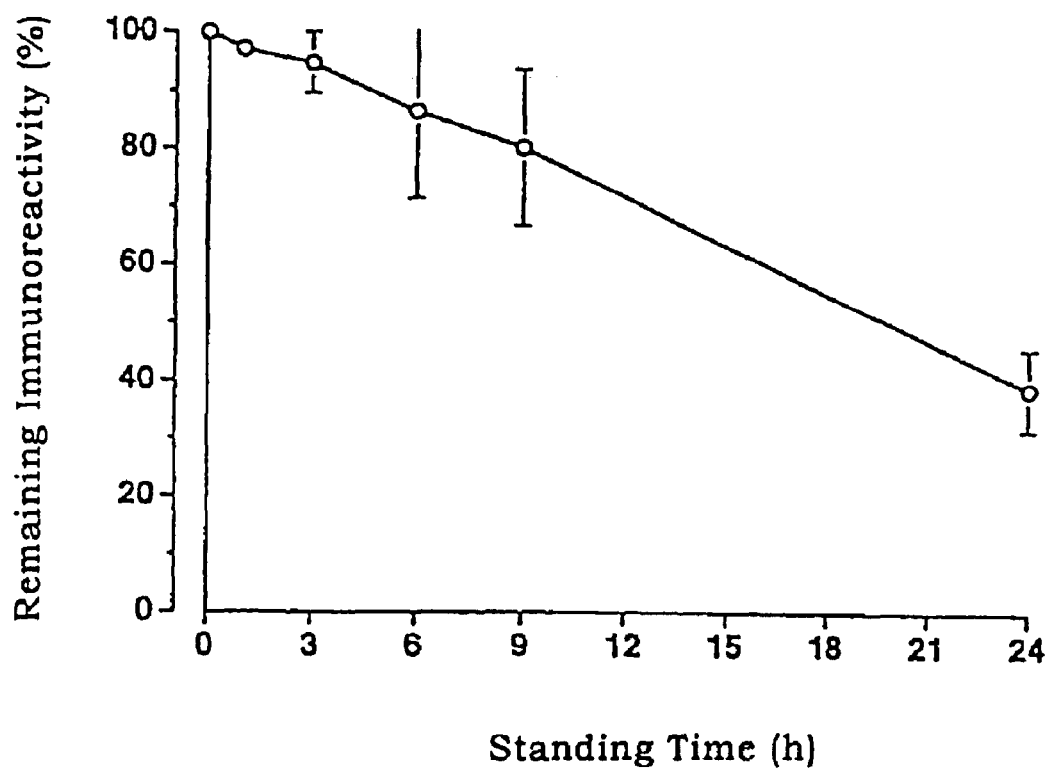
FIG. 5 is a graph showing the relationships between the storing time and BNP immunoreactivity of α-BNP kept in human plasma at 4° C.

The stability of γ-BNP derivatives and α-BNP in plasma samples are shown in FIGS. 4 and 5, respectively.

From FIG. 4, it is revealed that γ-BNP derivatives do not lose significantly the immunoreactivity compared with the initial activity even after 24-hour-standing at 25° C. From FIG. 5, by contrast, it is revealed that α-BNP loses the immunoreactivity to about 40% based on the initial activity after 24-hour-standing at 4° C.

The above results demonstrate that α-BNP is far less stable compared with γ-BNP derivative in blood and that the latter is much more suited in the diagnosis of cardiac diseases than the former.

INDUSTRIAL APPLICABILITY

As mentioned above, the BNP level in patients of heart failure sometimes increases to several tens times to several hundreds times of that of healthy normal subjects, and the change of BNP in the cases of heart failure is so marked that no other hormones are incomparable therewith. For this reason, the usefulness of BNP measurement has been proposed.

The immunoassay of the present invention allows to determine specifically γ-BNP derivatives without measuring α-BNP. Accordingly, the present immunoassay can be a clinically significant means for diagnosis and prognostic monitoring of heart failure, which leads to conclusion/judgment somehow different from those resulted from conventional BNP assay.

Further, it is herein disclosed for the first time that γ-BNP, which is a target substance to be assayed by the present method, is stable in blood. Therefore, immunoassay of the present invention provides stable and reliable clinical data without being affected by the process of collecting or storing samples, or the time from the collection until measurement. Further, the immunoassay of the present invention does not require any special pretreatments of blood sample and therefore gives clinical data conveniently, thereby contributing to the establishment of highly accurate diagnosis of cardiac diseases.

---

What is claimed is:

1. A sandwich immunoassay, which is specific for detecting human γ-brain natriuretic peptide (γ-BNP) having a carboxy terminus portion including α-BNP and having an amino terminus portion which does not include α-BNP, said sandwich immunoassay comprising:
   (a) an immunoassay solution,
   (b) a first antibody in said immunoassay solution, said first antibody being specifically reacted with the carboxy terminus portion of a human γ-BNP, and
   (c) a second antibody in said immunoassay solution, said second antibody being specifically reacted with the amino terminus portion of said human γ-BNP and which is not reacted with the carboxy terminus portion of said human γ-BNP.

2. The sandwich immunoassay of claim 1, wherein said human γ-BNP comprises the amino acid sequence of amino acid Nos. 27–134 of SEQ ID NO: 2.

3. The sandwich immunoassay of claim 1, wherein said second antibody is reacted with the amino acid sequence of amino acid Nos. 27–102 of SEQ ID NO: 2.

4. The sandwich immunoassay of claim 1, wherein said human γ-BNP comprises the amino acid sequence encoded by the nucleic acid sequence of nucleic acid Nos. 79–402 of SEQ ID NO: 1.

5. The sandwich immunoassay of claim 1, wherein said second antibody is reacted with the amino acid sequence encoded by the nucleic acid sequence of nucleic acid Nos. 79–306 of SEQ ID NO: 1.

6. The sandwich immunoassay of claim 1, wherein at least one of said first antibody and said second antibody is labeled with a detectable label or is immobilized.

7. The sandwich immunoassay of claim 6, wherein said detectable label is a radioactive isotope, an enzyme, a fluorescent substance, a luminescent substance, or a particle.

8. A sandwich immunoassay kit, which is specific for detecting human γ-BNP having a carboxy terminus portion including α-BNP and having an amino terminus portion which does not include α-BNF, said sandwich immunoassay kit comprising:
   (a) as a first component, a first antibody which is specifically reactive with the carboxy terminus portion of a human γ-BNP, and
   (b) as a second component, a second antibody which is specifically reactive with the amino terminus portion of said human γ-BNP and which is not specifically reactive with the carboxy terminus portion of said human γ-BNP.

9. The sandwich immunoassay kit of claim 8, wherein said human γ-BNP comprises the amino acid sequence of amino acid Nos. 27–134 of SEQ ID NO: 2.

10. The sandwich immunoassay kit of claim 8, wherein said second antibody is reacted with the amino acid sequence of amino acid Nos. 27–102 of SEQ ID NO: 2.

11. The sandwich immunoassay kit of claim 8, wherein at least one of said first antibody and said second antibody is labeled with a detectable label or is immobilized.

12. The sandwich immunoassay kit of claim 11, wherein said detectable label is a radioactive isotope, an enzyme, a fluorescent substance, a luminescent substance, or a particle.

13. The sandwich immunoassay kit of claim 11, which further comprises a means for detecting the label.

14. The sandwich immunoassay kit of claim 8, wherein at least one of said first antibody and said second antibody is a monoclonal antibody.

15. The sandwich immunoassay kit of claim 8, wherein at least one of said first antibody and said second antibody is a polyclonal antibody.

16. A method for assaying for human γ-BNP having a carboxy terminus portion including α-BNP and having an amino terminus portion which does not include α-BNP, comprising the steps of:

contacting a sample solution to be assayed with a first antibody, said first antibody specifically reacting with the carboxy terminus portion of a human γ-BNP and contacting the sample solution with a second antibody, said second antibody specifically reacting with the amino terminus portion of said human γ-BNP and not reacting with the carboxy terminus portion of said human γ-BNP, and measuring the amount of human γ-BNP in the sample solution to which the first antibody and the second antibody is reacted.

17. The method of claim 16, wherein at least one of said first antibody and said second antibody is labeled with a detectable label or is immobilized.

18. The method of claim 16, wherein said detectable label is a radioactive isotope, an enzyme, a fluorescent substance, a luminescent substance, or a particle.

19. The method of claim 16, wherein at least one of said first antibody and said second antibody is a monoclonal antibody.

20. The method of claim 16, wherein at least one of said first antibody and said second antibody is a polyclonal antibody.

* * * * *

SEQUENCE LISTING

<160> NUMBER OF SEQ ID NOS: 2

<210> SEQ ID NO 1
<211> LENGTH: 402
<212> TYPE: DNA
<213> ORGANISM: human

<400> SEQUENCE: 1

```
atg gat ccc cag aca gca cct tcc cgc gcg ctc ctg ctc ctg ctc ttc      48
Met Asp Pro Gln Thr Ala Pro Ser Arg Ala Leu Leu Leu Leu Leu Phe
1               5                   10                  15 ttg cat ctg gct ttc ctg gga ggt cgt tcc cac ccg ctg ggc agc ccc      96
Leu His Leu Ala Phe Leu Gly Gly Arg Ser His Pro Leu Gly Ser Pro
            20                  25                  30 ggt tca gcc tcg gac ttg gaa acg tcc ggg tta cag gag cag cgc aac     144
Gly Ser Ala Ser Asp Leu Glu Thr Ser Gly Leu Gln Glu Gln Arg Asn
        35                  40                  45 cat ttg cag ggc aaa ctg tcg gag ctg cag gtg gag cag aca tcc ctg     192
His Leu Gln Gly Lys Leu Ser Glu Leu Gln Val Glu Gln Thr Ser Leu
    50                  55                  60 gag ccc ctc cag gag agc ccc cgt ccc aca ggt gtc tgg aag tcc cgg     240
Glu Pro Leu Gln Glu Ser Pro Arg Pro Thr Gly Val Trp Lys Ser Arg
65                  70                  75                  80 gag gta gcc acc gag ggc atc cgt ggg cac cgc aaa atg gtc ctc tac     288
Glu Val Ala Thr Glu Gly Ile Arg Gly His Arg Lys Met Val Leu Tyr
                85                  90                  95 acc ctg cgg gca cca cga agc ccc aag atg gtg caa ggg tct ggc tgc     336
Thr Leu Arg Ala Pro Arg Ser Pro Lys Met Val Gln Gly Ser Gly Cys
            100                 105                 110
```

-continued

```
ttt ggg agg aag atg gac cgg atc agc tcc tcc agt ggc ctg ggc tgc     384
Phe Gly Arg Lys Met Asp Arg Ile Ser Ser Ser Ser Gly Leu Gly Cys
        115                 120                 125 aaa gtg ctg agg cgg cat                                              402
Lys Val Leu Arg Arg His
    130             134

<210> SEQ ID NO 2
<211> LENGTH: 134
<212> TYPE: PRT
<213> ORGANISM: human

<400> SEQUENCE: 2

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Ser Gly Leu Gly Cys
        115                 120                 125

Lys Val Leu Arg Arg His
    130             134
```